United States Patent
Haider (10) Patent No.: US 8,469,887 B2
(45) Date of Patent: Jun. 25, 2013

(54) METHOD AND APPARATUS FOR FLOW PARAMETER IMAGING

(75) Inventor: Bruno H. Haider, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 3085 days.

(21) Appl. No.: 10/742,283

(22) Filed: Dec. 19, 2003

(65) Prior Publication Data

US 2005/0137479 A1    Jun. 23, 2005

(51) Int. Cl.
*A61B 8/00* (2006.01)

(52) U.S. Cl.
USPC .......................................................... 600/437

(58) Field of Classification Search
USPC ...................... 600/441, 472; 382/128; 73/597
See application file for complete search history.

(56) References Cited

U.S. PATENT DOCUMENTS

| | | | | |
|---|---|---|---|---|
| 4,893,283 A | * | 1/1990 | Pesque | 367/7 |
| 5,623,930 A | * | 4/1997 | Wright et al. | 600/456 |
| 5,860,924 A | * | 1/1999 | Quistgaard | 600/441 |
| 5,935,074 A | * | 8/1999 | Mo et al. | 600/454 |
| 6,023,968 A | * | 2/2000 | Spratt et al. | 73/204.14 |
| 6,221,020 B1 | * | 4/2001 | Lysyansky et al. | 600/453 |
| 6,322,511 B1 | * | 11/2001 | Guracar et al. | 600/453 |
| 6,618,493 B1 | * | 9/2003 | Torp et al. | 382/131 |
| 2003/0100833 A1 | * | 5/2003 | He et al. | 600/446 |
| 2003/0125624 A1 | * | 7/2003 | Shiki | 600/443 |

FOREIGN PATENT DOCUMENTS

| | | |
|---|---|---|
| JP | 7008492 A | 1/1995 |
| JP | 11221217 A | 8/1999 |
| JP | 2002224114 A | 8/2002 |
| JP | 2003284718 A | 10/2003 |
| JP | 2003310612 A | 11/2003 |
| WO | WO0057766 | * 10/2000 |

* cited by examiner

Primary Examiner — Parikha Mehta
(74) Attorney, Agent, or Firm — Marie-Claire B. Maple (57) ABSTRACT

A method and an apparatus for performing pulsed-wave spectral Doppler imaging at every color flow range gate location in a two-dimensional (or three-dimensional) region of interest. Spectral processing is necessary to determine the flow parameters. Performing this processing at every color flow range gate location creates the two-dimensional image. The method generates two-dimensional images of flow parameters such as peak velocity, pulsatility index, resistance index, etc. With the two-dimensional image, the user immediately observes where the most critical value of the flow parameter occurs and what that value is.

17 Claims, 4 Drawing Sheets

METHOD AND APPARATUS FOR FLOW PARAMETER IMAGING

BACKGROUND OF THE INVENTION

This invention generally relates to methods and apparatus for ultrasonic imaging of blood flow parameters.

The most common modes of diagnostic ultrasound imaging include B- and M-modes (used to image internal, physical structure), spectral Doppler, and color flow (the latter two primarily used to image flow characteristics, such as in blood vessels). The color flow mode is typically used to detect the velocity of blood flow toward/away from the transducer, and it essentially utilizes the same technique as is used in the spectral Doppler mode. Whereas the spectral Doppler mode displays velocity versus time for a single selected sample volume, color flow mode displays hundreds of adjacent sample volumes simultaneously, all laid over a B-mode image and color-coded to represent each sample volume's velocity.

Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. Alternatively, in power Doppler imaging, the power contained in the returned Doppler signal is displayed.

Conventional ultrasound imaging systems comprise an array of ultrasonic transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. In the case of a steered array, by changing the time delays and amplitudes of the applied voltages, the beam with its focal point can be moved in a plane to scan the object. In the case of a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delays (and/or phase shifts) and gains to the signal from each receiving transducer element.

A single scan line (or small localized group of scan lines) is acquired by transmitting focused ultrasound energy at a point, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

A B-mode ultrasound image is composed of multiple image scan lines. The brightness of a pixel is based on the intensity of the echo return from the biological tissue being scanned. The outputs of the receive beamformer channels are coherently summed to form a respective pixel intensity value for each sample volume in the object region or volume of interest. These pixel intensity values are log-compressed, scan-converted and then displayed as a B-mode image of the anatomy being scanned.

In addition, ultrasonic scanners for detecting blood flow based on the Doppler effect are well known. Such systems operate by actuating an ultrasonic transducer array to transmit ultrasonic waves into the object and receiving ultrasonic echoes backscattered from the object. The sequence of transmitting waves and receiving echo signals is repeated several times for the same scan line and focal positions. The set of echo signals resulting from identical acquisitions is referred to as an ensemble. Since the ensemble is comprised of beams with identical beamforming the only difference among the beams is the information about the position of the scatterers. Position changes of the scatterers translate into phase shifts in the received signals. The phase shifts further translate into the velocity of the blood flow. The blood velocity is calculated by measuring the phase shift from firing to firing at a specific range gate.

Color flow images are produced by superimposing a color image of the velocity of moving material, such as blood, over a black and white anatomical B-mode image. Typically, color flow mode displays hundreds of adjacent sample volumes simultaneously laid over a B-mode image, each sample volume being color-coded to represent velocity of the moving material inside that sample volume at the time of interrogation.

In state-of-the-art ultrasonic scanners, the pulsed or continuous wave Doppler waveform is also computed and displayed in real-time as a gray-scale spectrogram of velocity versus time with the gray-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

The color flow and spectral Doppler techniques have their respective advantages and shortcomings. The color flow Doppler technique displays the mean and possibly the variance of the local blood flow velocity from a region of interest. The velocity information is color coded and overlaid onto an anatomical grayscale image. Flow abnormalities can be observed easily due to the two-dimensional display of the flow distribution. The shortcoming of color flow Doppler imaging is that only the mean velocity and variance can be determined. More advanced parameters such as peak velocity, resistance index, and pulsatility index cannot be assessed using color flow Doppler imaging. Further, the time resolution of color flow Doppler imaging is limited by its frame rate. Typical values are in the range of 50 to 100 msec. In comparison, tracking the systolic flow in the beating heart requires a time resolution of 10 to 20 msec.

In low-flow situations the color flow frame rate can be increased by interleaving pulses in two or more directions. In this scheme two or more color flow ensembles are formed simultaneously by sending consecutive pulses into the ensemble directions before repeating the sequence and sending another pulse into the first direction.

Spectral Doppler ultrasound imaging acquires flow information from a single location at a much higher rate and for a longer period of time. Pulses are transmitted and received at the PRF (pulse repetition frequency), which can be 1000 times higher than the frame rate in color flow imaging. Further the acquisition of spectral data for a given location is continuous, i.e., not disrupted by the acquisition of data in the many other locations needed to form a 2-D image. The continuous acquisition spectral Doppler samples allows one to calculate the entire Doppler spectrum (as opposed to only the mean and variance in color flow imaging). Diagnostic information is extracted from the shape of the spectrum as well as spectral changes during the cardiac cycle. For example, the peak velocity can be determined as a function of time, yielding critical information for the staging of vascular stenoses or cardiac valve regurgitations. An example of the evaluation of spectral changes is the determination of the "resistance index" and the "pulsatility index". These indices are determined by relating the peak velocities at two different times within the cardiac cycle (end systole and end diastole). Current color flow imaging techniques cannot determine such indices because the time resolution is too poor and the exact spectral shape is unknown. The disadvantage of spectral Doppler imaging, however, is that the flow parameters are determined at only a single spatial location. The spatial distribution of the flow parameters is not easily accessible. In fact, it can only be determined by repeatedly performing the spectral measurements at different locations. However, such an approach is inaccurate, time consuming and expensive, i.e., undesirable.

There is a need for a method that will allow spectral Doppler processing to be performed at every color flow range gate location to create a two-dimensional image.

BRIEF DESCRIPTION OF THE INVENTION

The present invention is directed to a method and an apparatus for performing pulsed-wave spectral Doppler imaging at every color flow range gate location in a two-dimensional (or three-dimensional) region of interest. Spectral processing is necessary to determine the flow parameters. Performing this processing at every color flow range gate location creates the two-dimensional image. The method disclosed herein generates two-dimensional images of flow parameters such as peak velocity, pulsatility index, resistance index, etc. With the two-dimensional image, the user immediately observes where the most critical value of the flow parameter occurs and what that value is.

One aspect of the invention is a method for ultrasonic flow parameter imaging comprising the following steps: (a) transmitting a sequence of spatially diverging ultrasonic transmit beams from a transducer array into a region of interest in a body at a pulse repetition frequency; (b) converting ultrasound wave energy, returned along respective lines to the transducer array from respective spatial positions in the body in the path of the transmit beams, into electronic signals representing respective receive beams following each transmission; (c) calculating a respective value of a given flow parameter for each receive beam, a respective set of flow parameter values being calculated for each transmission; and (d) displaying a respective visual value for each calculated flow parameter value in a spatial relationship that generally corresponds to the spatial relationship of the spatial positions in the body, thereby forming a respective flow parameter image following each transmission.

Another aspect of the invention is an imaging system comprising: an array of transducer elements; a display subsystem; means for controlling the transducer array to transmit a sequence of spatially diverging ultrasonic transmit beams into a region of interest at a pulse repetition frequency; means for organizing electronic signals from the transducer array into a respective set of receive beams of acoustic data after each transmit, the receive beams of each set being a function of ultrasound wave energy returned along respective lines to the transducer array from respective spatial positions in the body in the path of the transmit beams; means for calculating a respective value of a given flow parameter for each receive beam, a respective set of flow parameter values being calculated for each transmission; and means for controlling the display monitor to display a respective visual value for each calculated flow parameter value in a spatial relationship that generally corresponds to the spatial relationship of the spatial positions in the body, thereby forming a respective flow parameter image following each transmission.

A further aspect of the invention is an imaging system comprising: an array of transducer elements; a transmitter programmed to activate the transducer array to transmit a sequence of spatially diverging ultrasonic transmit beams into a region of interest at a pulse repetition frequency; a receiver programmed to organize electronic signals from the transducer array into a respective set of receive beams of acoustic data after each transmit, the receive beams of each set being a function of ultrasound wave energy returned along respective lines to the transducer array from respective spatial positions in the body in the path of the transmit beams; an estimator for calculating a respective value of a given flow parameter for each receive beam, a respective set of flow parameter values being calculated for each transmission; a converter for converting the sets of flow parameter values into respective sets of pixel data; a display monitor; and a controller for controlling the display monitor to display each set of pixel data to form a respective flow parameter image following each transmission.

Yet another aspect of the invention is an imaging system comprising: a display subsystem; an array of transducer elements; programmable electronic circuitry for operatively controlling the display subsystem and the array of transducer elements and programmed to perform the following steps: controlling the transducer array to transmit a sequence of spatially diverging ultrasonic transmit beams into a region of interest in a body at a pulse repetition frequency; organizing electronic signals from the transducer array into a respective set of receive beams of acoustic data after each transmit, the receive beams of each set being a function of ultrasound wave energy returned along respective lines to the transducer array from respective spatial positions in the body in the path of the respective transmit beam; calculating a respective value of a given flow parameter for each receive beam, a respective set of flow parameter values being calculated for each transmission; and controlling the display monitor to display a respective visual value for each calculated flow parameter value in a spatial relationship that generally corresponds to the spatial relationship of the spatial positions in the body, thereby forming a respective flow parameter image following each transmission.

A further aspect of the invention is a method for ultrasonic flow parameter imaging comprising the following steps: (a) transmitting a sequence of wide ultrasonic transmit beams from a transducer array into a region of interest in a body at a pulse repetition frequency; (b) converting ultrasound wave energy returned to the transducer array into electronic acoustic data signals; (c) forming multiple versions of the acoustic data signals; (d) amplifying the acoustic data signals of the multiple versions; (e) applying a respective set of time delays to each version of acoustic data signals to form a respective set of receive beams for each transmission, the sets of time delays being independent of each other and being selected so that, for each transmission, each receive beam is derived from ultrasound wave energy returned along a respective line from a respective portion of the body in the path of the transmit beam; (f) calculating a respective value of a given flow parameter for each receive beam, a respective set of flow parameter values being calculated for each transmission; and (g) displaying a respective visual value for each calculated flow parameter value in a spatial relationship that generally corresponds to the spatial relationship of the spatial positions in the body, thereby forming a respective flow parameter image following each transmission.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

Figure 1:
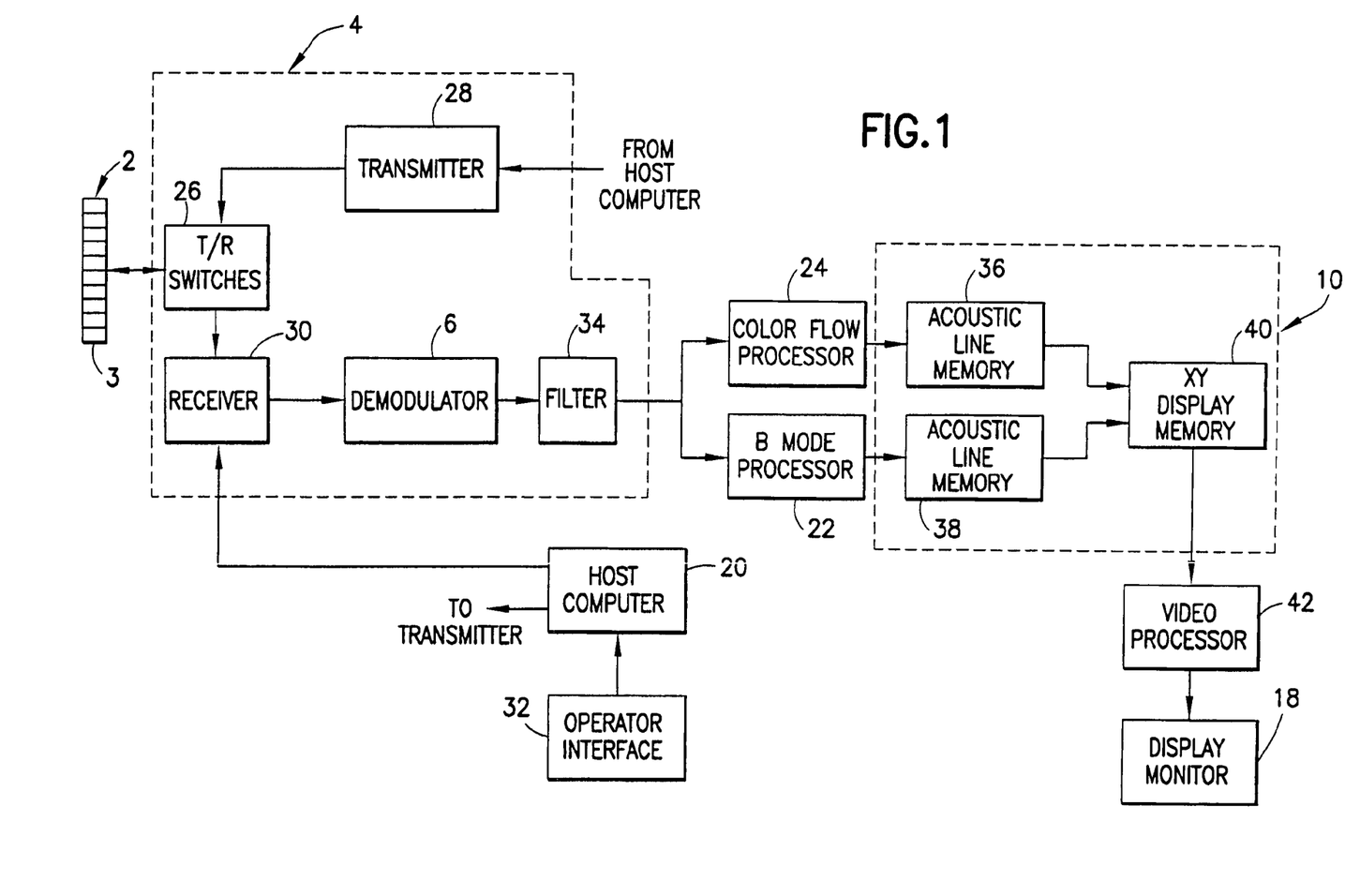
FIG. 1 is a block diagram showing the B mode and color flow mode signal processing chains for one known of ultrasound imaging system.

Referring to FIG. 1, a known ultrasound imaging system comprises a transducer array 2 consisting of a plurality of separately driven transducer elements 3. The transducer is connected to a beamformer 4 comprising a transmitter 28 and a receiver 30. In a transmit mode, a set of transmit/receive (T/R) switches 26 couple the transducer elements to transmitter 28. Each transducer element 3 produces a burst of ultrasonic energy when energized by a respective pulsed waveform produced by transmitter 28. In a receive mode, the T/R switches 26 couple the transducer elements to receiver 30. The ultrasonic energy reflected back to transducer array 2 from the object under study is converted to an analog electrical signal by each receiving transducer element 3 and applied separately to receiver 30. The transmitter and receiver are operated under control of a host computer (i.e., master controller) 20. The host computer 20 determines the conditions under which the acoustic pulses will be transmitted. The host computer can provide different sets of transmit sequences, transmit focus delays and transmit levels for B-mode and color flow mode imaging. A complete scan is performed by acquiring a series of echoes in which transmitter 28 is gated ON momentarily to energize each transducer element 3 in the transmit aperture, and the subsequent echo signals produced by each transducer element are applied to receiver 30. The receiver 30 converts the analog echo signals to digital signals and combines the respective digital signals derived from each transducer element to produce a single beamsummed signal which is used to produce a line in an image displayed by a display monitor 18.

Referring still to FIG. 1, in baseband imaging systems the beamsummed signal is output to a demodulator 6, which converts the beamsummed signal into baseband in-phase I and quadrature Q data vectors. The I and Q acoustic data vectors from the demodulator 6 are output to an FIR filter 34, which is provided with filter coefficients from a filter coefficient memory (not shown). The filter coefficient memory is programmed by the host computer 20.

The acoustic data from filter 34 is sent to a switch (not shown). In the B mode, acoustic data vectors acquired during scanning of an entire image frame are output to the B-mode processor 22. In the color flow mode, acoustic data vectors acquired during scanning of an ROI are output to a color flow processor 24. Depending on whether the acoustic data is for the background image or the ROI, the output of filter 34 is channeled to the appropriate processor.

In the B mode, the B-mode processor 22 detects the envelope of the streams of I and Q acoustic data and then log-compresses the respective signal envelopes. The envelope of a baseband signal is the magnitude of the vector which I and Q represent. The I,Q phase angle is not used in the B-mode display. The magnitude (i.e., intensity) of the signal is the square root of the sum of the squares of the orthogonal components, i.e., $(I^2+Q^2)^{1/2}$.

The B-mode intensity data is output to a B-mode acoustic line memory 38 in the scan converter 10. The acoustic line memory 38 accepts the processed vectors of B-mode intensity data acquired during scanning of the background area and interpolates where necessary. The acoustic line memory 38 also performs the coordinate transformation of the B-mode intensity data from polar coordinate (R-Ö) sector format or Cartesian coordinate linear format to appropriately scaled Cartesian coordinate display pixel intensity data. The pixel intensity data for background image area is written into an X-Y display memory 40.

The scan-converted B-mode image frame stored in the X-Y display memory 40 is passed to a video processor 42, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 18 for display.

System control is centered in a host computer 20, which accepts operator inputs through the operator interface 32 (e.g., a control panel) and in turn controls the various subsystems. The host computer 20 performs system level control functions. A system control bus (not shown) provides the interface from the host computer to the subsystems. The host computer preferably incorporates a scan controller (not shown in FIG. 1) which provides real-time (acoustic vector rate) control inputs to the various subsystems. The scan controller is programmed by the host computer CPU with the vector sequences and synchronization options for acoustic frame acquisitions. Thus, the scan controller controls the beam distribution and the beam density. The scan controller transmits the beam parameters defined by the host computer CPU to the subsystems via a scan control bus (not shown).

The B-mode images displayed by monitor 18 are produced from an image frame of data in which each datum indicates the intensity or brightness of a respective pixel in the display. Each pixel has an intensity value which is a function of the backscatter cross section of a respective sample volume in response to interrogating ultrasonic pulses and the gray map employed. The displayed image represents the tissue and/or blood flow in a scan plane through the body being imaged.

In the color flow mode, the color flow processor 24 converts the streams of I and Q acoustic data into color flow estimates of velocity or power. Given the angle è between the insonifying beam and the flow axis, the magnitude of the velocity vector can be determined by the standard Doppler equation:

$$v = cf_d/(2f_0 \cos \theta)$$

where c is the speed of sound in blood; $f_0$ is the transmit frequency; and $f_d$ is the motion-induced Doppler frequency shift in the backscattered ultrasound. The color flow processor 24 comprises a flow estimator that calculates the mean Doppler frequency, which is proportional to the velocity. Alternatively, the flow estimator may calculate a value that represents the power in the returned ultrasound echoes.

In one conventional ultrasound imaging system, the ultrasound transducer array 2 is activated to transmit a series of multi-cycle (typically 4-8 cycles) waveforms which are focused at the same transmit focal position with the same transmit characteristics. These waveforms are fired at a pulse repetition frequency (PRF). A series of transmit firings focused at the same transmit focal position are referred to as a "packet" or "ensemble". Each transmit beam propagates through the object being scanned and is reflected by ultrasound scatterers such as blood cells. The return signals are detected by the elements of the transducer array and then formed into a receive beam by receiver 30. This process is repeated for multiple points in a region of interest selected by the system operator via an operator interface 32.

The color flow estimates (i.e., power or velocity) are sent to a color flow acoustic line memory 36 of scan converter 46, which converts the color images into X-Y format for video display and stores the converted image in the X-Y display memory 40. The scan-converted color images are then passed to the video processor 42, which maps the video data to a display color map for video display. The color flow image data is then sent to the video monitor 18 for display in an ROI superimposed on the B-mode image data.

Figure 2:
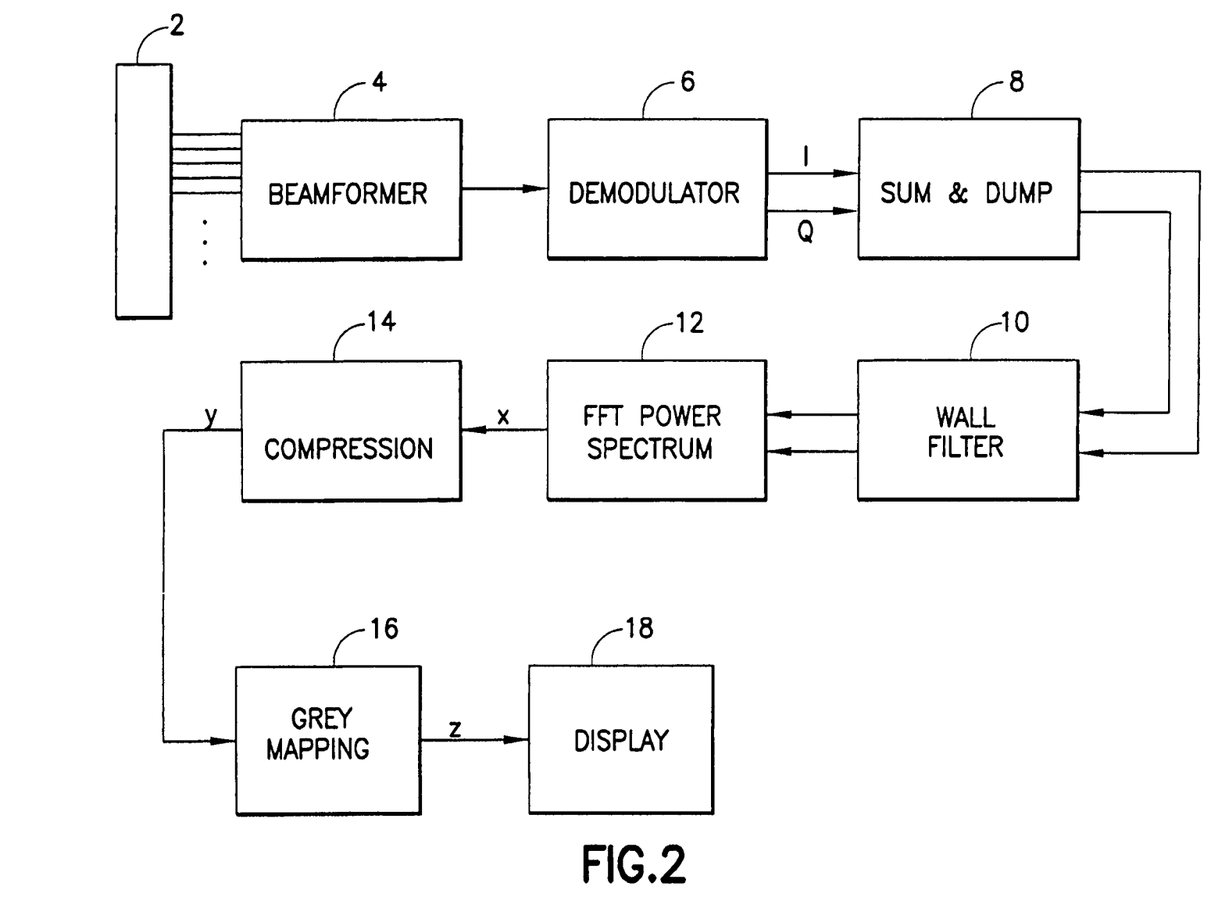
FIG. 2 is a block diagram of the basic signal processing chain in a conventional spectral Doppler imaging system.

A typical digital real-time ultrasonic imaging system having a spectral Doppler imaging mode is generally depicted in FIG. 2. An ultrasound transducer array 2 is activated by a transmitter of a beamformer 4 to transmit ultrasound beams focused at a desired transmit focal position. The transmitter provides a transmit ultrasound burst which is fired repeatedly at a pulse repetition frequency (PRF). The PRF is typically in the kilohertz range. The return RF signals are detected by the transducer elements and then formed into a receive beam by a receiver of beamformer 4. For a digital system, the summed (beamformed) RF signal from each firing is demodulated by demodulator 6 into its in-phase and quadrature (I/Q) components. The I/Q components are integrated (summed) over a specific time interval and then sampled by a "sum and dump" block 8. The summing interval and transmit burst length together define the length of the sample volume as specified by the user. The "sum and dump" operation effectively yields the Doppler signal backscattered from the sample volume. The Doppler signal is passed through a wall filter 10 which rejects any clutter in the signal corresponding to stationary or very slow-moving tissue. The filtered output is then fed into a spectrum analyzer 12, which typically takes the Fast Fourier Transform (FFT) over a moving time window of 64 to 256 samples. Each FFT power spectrum is compressed (block 14) and mapped (block 16) to a gray scale for display on monitor 18 as a single spectral line at a particular time point in the Doppler velocity (frequency) versus time spectrogram.

The components depicted in FIGS. 1 and 2 as well as the present invention can be incorporated in one and the same ultrasound imaging system, each imaging mode being selectable by the system user via the operator interface.

The innovative method disclosed herein combines the advantages of color flow imaging and spectral Doppler imaging by acquiring Doppler samples over the entire two-dimensional (or three-dimensional) region of interest at the pulse repetition frequency. At the PRF interval, spatially diverging transmit pulses are sent out. Unlike in color flow imaging, these transmit pulses are identical without any pulse-to-pulse or ensemble-to-ensemble steering changes. Therefore, the pulses must cover the entire region of interest. A highly parallel receive beamformer acquires all ultrasound lines within the region of interest, again at the PRF rate. This beamformer then provides Doppler samples at all spatial locations at the PRF. The flow parameter estimator then performs spectral processing for each of the multiple acquired receive beams.

The requirement for spectral processing—a sufficiently high rate of acquisition of Doppler samples—is met by the method disclosed herein, and therefore, all the flow parameters (peak velocity, resistance and pulsatility indices, etc.) can be determined for the entire region of interest. The user selects a particular flow parameter and a color-coded representation of that parameter is overlaid onto the anatomical grayscale (e.g., B mode) image. This display mechanism is very similar to conventional color flow with the exception that the displayed parameter can be any one of the spectral flow parameters.

The ultrasound beam characteristics of a conventional color flow or spectral Doppler beam are different from the ones acquired with the method disclosed herein. To achieve a wide transmit beam (covering the entire region of interest), no transmit beamforming is applied. The entire beam shaping is accomplished by the receive beamformer. Consequently, the beam will be wider and with higher side lobes. The increase in beamwidth can be compensated with a larger receive aperture; but the increased side lobes remain. However, it should be realized that the typical side-lobe levels of a conventional system, provided by the combination of transmit and receive beamforming, are most significant in B-mode imaging. Doppler applications tolerate much higher side-lobe levels, typically 20 to 25 dB below the main lobe. This observation is supported by steered Doppler imaging using linear arrays. The element pitch in such arrays is selected so that the grating lobe (a type of side lobe) is within the range stated above: Therefore, the increased side-lobe levels resulting from receive only beamforming can be tolerated.

Figure 3:
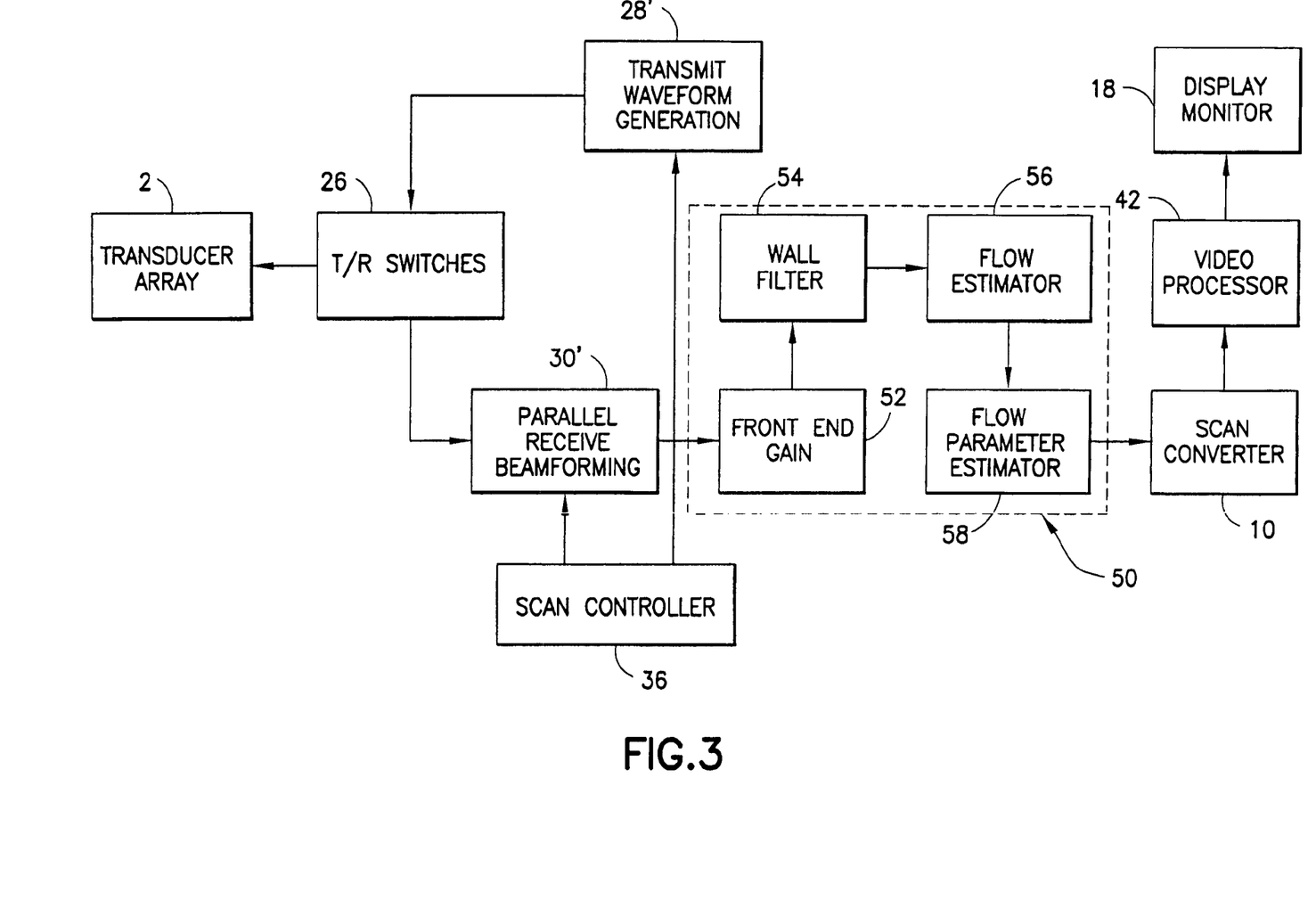
FIG. 3 is a block diagram showing portions of a system for implementing spectral Doppler imaging over an entire region of interest at the pulse repetition frequency in accordance with one embodiment of the present invention.

One embodiment of a system for implementing spectral Doppler imaging by acquiring Doppler samples over the entire region of interest at the pulse repetition frequency is depicted in FIG. 3. The scan controller 36 controls the transmitter 28' and the receiver 30'. In the transmit mode, the pulsers of the transmitter 28' are coupled to the transducers of array 2 via respective T/R switches 26. The transmit waveform is generated without beamforming, the result being that the transducer array 2 will transmit a multiplicity of spatially diverging pulses. In the receive mode, the receive beamformer 30' forms multiple receive beams for each transmit beam using parallel receive beamforming.

In standard, single-line receive beamforming, the incoming signal from each transducer element passes through the T/R switches to the receive beamformer (item 30 in FIG. 1). In the receive beamformer, the detected signal from each transducer element is individually amplified and delayed. At the output of the receive beamformer the delayed signals are summed to form the "beamsum signal" representing the receive beam. For each transmit beam going out, there is a respective beamsum signal formed from the echoes coming back. That beamsum signal can then be processed to derive amplitude information. Both the transmit beam and receive beam are synchronously swept (steered) across the image scene or target. Both beams are tightly focused to provide high spatial resolution.

In parallel receive beamforming, a wider transmit beam is created and multiple receive beams are formed within the spatial extent of the wide transmit beam. The parallel receive beamformer 30' (see FIG. 3) gets the same input signals as the standard beamformer and amplifies each one of these signals, but creates multiple delayed versions of each input under the control of the scan controller 36. For example, assume that the parallel receive beamformer 30' forms N delayed versions of every input. From the N versions, the beamsummer (part of the beamformer) creates N beamsum signals by summing all of the first versions, summing all of the second versions, and so forth. Since the N versions have independent delays, their beam directions can be different. This technique is practical only for regions where the wide transmit beam provides sufficient signal power.

The result is that for every transmit, one can acquire N receive beams. If the transmit beam is wide enough to illuminate the entire target scene, then the image could be formed with a single transmit event. One disadvantage of such an arrangement is reduced spatial resolution since the transmit is wide and no longer contributes to the beam focusing; another disadvantage is the increased complexity of the receive beamformer due to the replication of the delay and summing stages.

For parallel receive beamforming to be feasible, a wide transmit beam is required. To have a very large number of parallel receive beams, a spatially diverging transmit beam is needed. This transmit beam can be created, e.g., by having a small transmit aperture (the beamwidth is inversely proportional to the aperture size) In this case, the transmit delays should all be constant, Alternatively, a spherical delay pattern can be used to create a virtual focal point inside of the probe (normally the focus is in front of the probe). In either case, the transmitter 28' operates in accordance with mode control signals sent by the scan controller 36. These control signals dictate the aperture, focus and steering of the transmit waveform generated by the transmitter.

Each receive beam comprises a string of acoustic data samples, which are sent to a color flow processor 50 for color flow or flow parameter imaging. FIG. 3 illustrates four functional blocks that are contained within the color flow processor 50.

The color flow processor 50 may include a front end amplifier section 52 that increases the amplitude of the acoustic data samples, followed by a wall filter 54 that suppresses acoustic data samples derived from tissue and passes acoustic data samples derived from blood flow. The amplified signals derived from blood flow are then passed to the flow estimator 56, which determines a frequency shift or velocity estimate of the blood flow. The flow estimator 56 then sends the velocity or frequency shift information to the flow parameter estimator 58, which calculates an estimated pulsatility or resistance index. The resulting index values are then mapped to an appropriate color value (by a color mapping not shown in FIG. 3) and sent to a color acoustic line memory in the scan converter 10.

For each receive beam, the color flow processor 50 performs flow estimation (e.g., determines the mean velocity of the blood flow) in conventional fashion, and then performs flow parameter estimation based on the results of the flow estimation. These calculations are done for each receive beam, i.e., for each spatial position in the region of interest where a respective receive beam was focused.

Either the pulsatility index or the resistance index can be estimated by the flow parameter estimator 58. The estimate is used to generate a color to distinguish different pulsatility or resistance ranges. These ranges may include those that are typically found in veins or arteries in order to discriminate between them.

Figure 5:
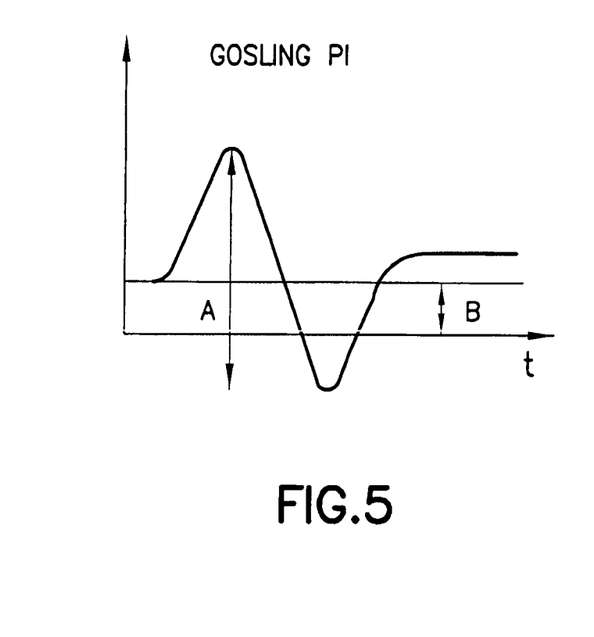
FIG. 5 is a diagram of a waveform labeled with parameters used to estimate a resistance index.

A pulsatility index (PI) may be defined by the equation PI=A/B (according to Gosling), where A is the peak systolic velocity minus the maximum diastolic velocity, and B is the time-averaged mean velocity. FIG. 5 depicts a cardiac waveform with the parameters A and B indicated thereon. The values used in the computation of the pulsatility index may be either frequencies or velocities since the determined ratio will be unaffected by the correction angle. Thus the pulsatility index is entirely angle independent, unlike traditional Doppler ultrasound.

Figure 4:
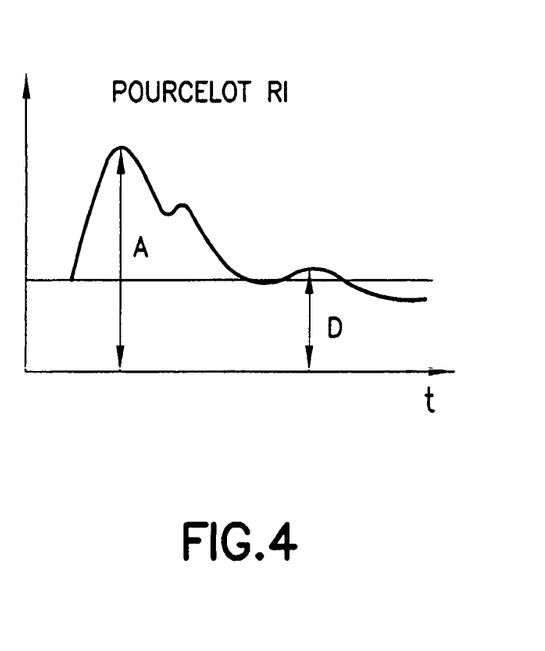
FIG. 4 is a diagram of a waveform labeled with parameters used to estimate a pulsatility index.

A resistance index (RI) may be defined by the equation RI=(A−D)/A (according to Pourcelot), where A is the peak systole and D is end diastole. FIG. 4 depicts a cardiac waveform with the parameters A and D indicated thereon. Again the values used in the computation of the resistance index may be either frequencies or velocities The flow parameter estimator 58 receives mean velocities as a function of time from the flow estimator 56. The flow estimator 56 then determines positive and negative peaks as well as the mean over a cardiac cycle. The pulsatility index is estimated by calculating the ratio of the variation over the average for the velocity estimates. The resistance index can be estimated by calculating the ratio of the unipolar variation over the maximum average. The variation is the difference between the peak and minimum values of the mean velocity over the cardiac cycle. More details concerning the foregoing computations can be found in U.S. Pat. No. 6,023,968 entitled "Real-Time Two-Dimensional Resistance and Pulsatility Mapping". All of these flow estimates are calculated over one cardiac cycle.

The essential distinction between the foregoing indices and regular flow estimates is that each index, as a single value, is calculated using all the flow estimates of cardiac cycle while flow estimate themselves change over the cardiac cycle.

In accordance with the embodiment disclosed herein, the system depicted in FIG. 3 continuously calculates the flow estimate at all pixel locations without any gaps in time large enough to cause the peak to be missed, thereby avoiding large errors in the index calculation. However, the flow parameter transmits can be interleaved with B-mode vector transmits to form one flow parameter image for each B-mode grayscale image, the former being superimposed or overlaid on the latter.

Compared to a conventional ultrasound system, the system described here has two distinct features. First, the receive beamformer is highly parallel since all receive beams must be acquired for every transmitted pulse. Second, the Doppler signal processing has increased requirements on computing power since the spectral flow parameters must now be calculated for a large number of spatial locations. Both of these problems can be attacked from two sides. First, advances in VLSI processing provide for significantly higher computing power than previously available. Second, many clinical applications do not require the high data rate that is afforded by spectral Doppler. Reducing the data rate to what is really required for a particular range of blood flow velocities will reduce the computing requirements.

If the region of interest is too large to be covered by a single transmit pulse, a technique similar to the color flow interleave mode can be applied. For flow estimation, the system uses beams with identical spatial characteristics (i.e. identical transmit and receive delays) that interrogate the target several times with distinct time intervals between pulses. The group of beams that scans the same direction over a period of time is called an "ensemble". Typically 4 to 16 pulses per ensemble are required to form a good flow estimate. The time interval between the pulses of an ensemble is the pulse repetition interval (PRI). The optimal PRI depends on the flow speed to be measured. Faster speeds require shorter PRIs (since one needs to sample the flow more often in a given time interval to measure its characteristics). For very slow flows, one needs very long PRIs. The time needed to acquire one image frame is the PRI times the number of pulses in the ensemble times the number of distinct beam directions. If the PRI is much longer than what is required for the round-trip propagation of the ultrasound wave, then multiple ensembles can be acquired in parallel. For example, for three different ensembles A, B, C of pulses transmitted in three different directions, one could acquire the returned echoes for the first pulse of ensemble A, then the first pulse of ensemble B, then the first pulse of ensemble C, then the second pulse of ensemble A, then the second pulse of ensemble B, then the second pulse of ensemble C, and so forth. This is an example of so-called "3× interleaving" since three ensembles are acquired in parallel. The frame rate would be 3× higher than without interleaving. In alternative embodiments of the present invention, splitting the region of interest into two or more sectors and sending consecutive pulses to each one of these sectors means that the transmit pulse only needs to cover the width of the subsector. Similar to the color flow interleave mode, this will reduce the maximum flow velocity that can be detected.

The disclosed method is applicable to medical ultrasonic imaging. Its benefit is the two- or three-dimensional measurement and display of flow parameters. This multi-dimensional display enhances the efficiency and accuracy of the medical examination. The method combines the advantages of color flow and spectral Doppler imaging without incurring their respective disadvantages.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A method for ultrasonic flow parameter imaging comprising the following steps:

transmitting a timed sequence of spatially diverging ultrasonic transmit beams from a transducer array into a region of interest in a body at a pulse repetition frequency;

converting ultrasound wave energy returned to said array into electronic signals;

beamforming said electrical signals to simultaneously form a respective set of multiple receive beams following transmission of each transmit beam, each set of receive beams consisting of multiple lines through respective spatial positions in the region of interest;

calculating a respective mean velocity value for each receive beam;

calculating a respective value of a given flow parameter for each receive beam, a respective set of flow parameter values being calculated from the respective set of mean velocity values; and displaying a respective visual value for each calculated flow parameter value in a spatial relationship that generally corresponds to the spatial relationship of said spatial positions in said body, thereby forming a respective flow parameter image.

2. The method as recited in claim 1, wherein the time interval between successive mean velocity estimates is not greater than 50 msec and the respective time sequence of mean velocity values extends over a full cardiac cycle.

3. The method as recited in claim 1, wherein said given flow parameter is a peak velocity of flow in said body, respective calculated values representing the peak velocity over a full cardiac cycle at respective spatial positions in said body.

4. The method as recited in claim 1, wherein said given flow parameter is a pulsatility index of flow in said body, respective calculated values representing the pulsatility index over a full cardiac cycle at respective spatial positions in said body.

5. The method as recited in claim 1, wherein said given flow parameter is a resistance index of flow in said body, respective calculated values representing the resistance index over a full cardiac cycle at respective spatial positions in said body.

6. The method as recited in claim 1, further comprising the step of calculating a respective value of a mean velocity of flow for each receive beam, respective calculated values representing the cardiac cycle's mean velocity over a full cardiac cycle at respective spatial positions in said body, wherein the calculated values of the given flow parameter are respectively derived in part from the calculated values of the mean velocity.

7. The method as recited in claim 1, further comprising the step of displaying a sequence of grayscale images of the structure of a portion of said body that includes said spatial positions in said body, wherein each flow parameter image is superimposed in color over a grayscale image.

8. The method as recited in claim 1, wherein said spatial positions lie in or almost in a single plane.

9. The method as recited in claim 1, wherein said spatial positions are distributed in a three-dimensional space and do not lie in or almost in a single plane.

10. An imaging system comprising:

an array of transducer elements;

a display subsystem;

means for controlling said transducer array to transmit a sequence of spatially diverging ultrasonic transmit beams into a region of interest at a pulse repetition frequency;

means for beamforming electrical signals from said array of transducer elements to simultaneously form a respective set of multiple receive beams following transmission of each transmit beam, each set of receive beams consisting of multiple lines through respective spatial positions in the region of interest;

means for calculating a respective value of a given flow parameter for each receive beam, a respective set of flow parameter values being calculated over a full cardiac cycle; and means for controlling said display monitor to display a respective visual value for each calculated flow parameter value in a spatial relationship that generally corresponds to the spatial relationship of said spatial positions in said body, thereby forming a respective flow parameter image.

11. An imaging system comprising:

an array of transducer elements;

a transmitter programmed to activate said transducer array to transmit a sequence of spatially diverging ultrasonic transmit beams into a region of interest at a pulse repetition frequency;

a receiver programmed to beamform electrical signals from said array of transducer elements to simultaneously form a respective set of multiple receive beams following transmission of each transmit beam, each set of receive beams consisting of multiple lines through respective spatial positions in the region of interest;

a first estimator for calculating a respective mean velocity value;

a second estimator for calculating a respective value of a given flow parameter for each receive beam, a respective set of flow parameter values being calculated over a full cardiac cycle;

a converter for converting said sets of flow parameter values into respective sets of pixel data;

a display monitor; and a controller for controlling said display monitor to display each set of pixel data to form a respective flow parameter image.

12. The system as recited in claim 11, wherein the time interval between successive mean velocity estimates is not greater than 50 msec and the time sequence of mean velocity estimates ranges over a full cardiac cycle.

13. The system as recited in claim 11, wherein said given flow parameter is a peak velocity of flow in said body, respective calculated values representing the peak velocity over a full cardiac cycle at respective spatial positions in said body.

14. The system as recited in claim 11, wherein said given flow parameter is a pulsatility index of flow in said body, respective calculated values representing the pulsatility index over a full cardiac cycle at respective spatial positions in said body.

15. The system as recited in claim 11, wherein said given flow parameter is a resistance index of flow in said body, respective calculated values representing the resistance index over a full cardiac cycle at respective spatial positions in said body.

16. The system as recited in claim 11, wherein said given flow parameter is the cardiac cycle's mean velocity in said body, respective calculated values representing the mean velocity over a full cardiac cycle at respective spatial positions in said body.

17. The system as recited in claim 11, further comprising means for acquiring a respective set of receive beams of B mode acoustic data for each transmit that is a function of the structure of a portion of said body that includes said spatial positions in said body, wherein said controller further controls said display monitor to display a sequence of grayscale images of the structure of said portion of said body derived from said respective sets of receive beams of B mode acoustic data, wherein each flow parameter image is superimposed in color over a grayscale image.

* * * * *